US007744568B2

(12) United States Patent
Douglas et al.

(10) Patent No.: US 7,744,568 B2
(45) Date of Patent: *Jun. 29, 2010

(54) INFUSION HUB ASSEMBLY AND FLUID LINE DISCONNECT SYSTEM

(75) Inventors: Joel S. Douglas, Groton, CT (US); Robert L. Hugo, Gilroy, CA (US); Cynthia Zhang, Saratoga, CA (US)

(73) Assignee: ICU Medical, Inc., San Clemente, CA (US)

( * ) Notice: Subject to any disclaimer, the term of this patent is extended or adjusted under 35 U.S.C. 154(b) by 184 days.

This patent is subject to a terminal disclaimer.

(21) Appl. No.: 11/691,059

(22) Filed: Mar. 26, 2007

(65) Prior Publication Data

US 2008/0312598 A1 Dec. 18, 2008

Related U.S. Application Data

(63) Continuation of application No. 10/744,862, filed on Dec. 22, 2003, now abandoned, which is a continuation of application No. 10/091,123, filed on Mar. 4, 2002, now Pat. No. 6,685,674.

(60) Provisional application No. 60/299,842, filed on Jun. 19, 2001, provisional application No. 60/273,490, filed on Mar. 4, 2001.

(51) Int. Cl.
*A61M 5/178* (2006.01)

(52) U.S. Cl. .............................. 604/167.01; 604/164.01; 604/167.02; 604/167.03; 604/533; 604/539

(58) Field of Classification Search ............ 604/164.01, 604/164.11, 165.04, 167.01–167.05, 533, 604/534, 539

See application file for complete search history.

(56) References Cited

U.S. PATENT DOCUMENTS 3,502,097 A 3/1970 Muller (Continued)

FOREIGN PATENT DOCUMENTS

EP 0142222 8/1984

(Continued)

OTHER PUBLICATIONS

International Search Report of the International Searching Authority, mailed Mar. 20, 2003, in related international application No. PCT/US02/06701.

(Continued)

*Primary Examiner*—Kevin C Sirmons
*Assistant Examiner*—Bhisma Mehta
(74) *Attorney, Agent, or Firm*—Knobbe, Martens, Olson & Bear, LLP

(57) ABSTRACT

An infusion hub assembly, comprising: a hub received in a hole in a wing, the hub having a bore passing therethrough, with an upper portion of the circular hub having an attachment surface thereon; an infusion cannula extending downwardly away from the wing, the infusion cannula being in fluid communication with the bore passing through the hub; a cover having a bore passing therethrough and having an inner attachment surface adapted to mate with the attachment surface on the upper portion of the hub; and a septum positioned in alignment with the bore passing through the cover.

An infusion connector set comprising: a first connector; a septum received in the first connector; a second connector; a septum received in the second connector; and a flanged needle which penetrates both the septums in the first and second connectors when the first and second connectors are connected together.

17 Claims, 14 Drawing Sheets

U.S. PATENT DOCUMENTS

| | | |
|---|---|---|
| 3,861,972 A | 1/1975 | Glover et al. |
| 3,964,470 A | 6/1976 | Trombley |
| 3,986,508 A | 10/1976 | Barrington |
| 4,235,234 A | 11/1980 | Whitney et al. |
| 4,318,402 A | 3/1982 | Vaillancourt |
| 4,352,354 A | 10/1982 | Ujihara |
| 4,352,358 A | 10/1982 | Angelchik |
| D267,199 S | 12/1982 | Koenig |
| 4,362,156 A | 12/1982 | Feller, Jr. et al. |
| 4,511,359 A | 4/1985 | Vaillancourt |
| 4,531,937 A | 7/1985 | Yates |
| 4,576,211 A | 3/1986 | Valentini et al. |
| 4,619,247 A | 10/1986 | Inoue |
| 4,619,643 A | 10/1986 | Bai |
| 4,645,495 A | 2/1987 | Vaillancourt |
| 4,664,656 A | 5/1987 | Taddei |
| 4,713,057 A | 12/1987 | Huttner et al. |
| 4,723,947 A | 2/1988 | Konopka |
| 4,752,292 A | 6/1988 | Lopez et al. |
| 4,755,173 A | 7/1988 | Konopka et al. |
| 4,813,939 A | 3/1989 | Marcus |
| 4,863,432 A | 9/1989 | Kvalo |
| 4,944,728 A | 7/1990 | Carrell et al. |
| 4,950,260 A | 8/1990 | Bonaldo |
| 4,966,588 A | 10/1990 | Rayman et al. |
| 4,973,318 A | 11/1990 | Holm et al. |
| 5,078,689 A | 1/1992 | Keller |
| 5,084,015 A | 1/1992 | Moriuchi |
| 5,098,397 A | 3/1992 | Svensson et al. |
| 5,176,662 A | 1/1993 | Bartholomew et al. |
| 5,186,712 A | 2/1993 | Kelso et al. |
| 5,257,980 A | 11/1993 | Van Antwerp et al. |
| 5,267,967 A | 12/1993 | Schneider |
| 5,292,308 A | 3/1994 | Ryan |
| 5,334,188 A | 8/1994 | Inoue et al. |
| 5,338,314 A | 8/1994 | Ryan |
| 5,344,414 A | 9/1994 | Lopez et al. |
| 5,344,417 A | 9/1994 | Wadsworth, Jr. |
| 5,405,340 A | 4/1995 | Fageol et al. |
| 5,423,775 A | 6/1995 | Cannon |
| 5,487,728 A | 1/1996 | Vaillancourt |
| 5,501,676 A | 3/1996 | Niedospial et al. |
| 5,507,733 A | 4/1996 | Larkin et al. |
| 5,514,117 A | 5/1996 | Lynn |
| 5,522,803 A | 6/1996 | Teissen-Simony |
| 5,545,143 A | 8/1996 | Fischell |
| 5,545,152 A | 8/1996 | Funderburk et al. |
| 5,549,583 A | 8/1996 | Sanford et al. |
| 5,562,617 A | 10/1996 | Finch et al. |
| 5,584,813 A | 12/1996 | Livingston et al. |
| 5,591,188 A | 1/1997 | Waisman |
| D380,262 S | 6/1997 | Van Funderburk et al. |
| 5,637,098 A | 6/1997 | Bierman |
| 5,665,071 A | 9/1997 | Wyrick |
| 5,685,866 A | 11/1997 | Lopez |
| 5,688,254 A | 11/1997 | Lopez et al. |
| 5,702,371 A | 12/1997 | Bierman |
| 5,718,682 A | 2/1998 | Tucker |
| 5,722,959 A | 3/1998 | Bierman |
| 5,735,271 A | 4/1998 | Lorenzen et al. |
| 5,743,883 A | 4/1998 | Visconti |
| 5,776,116 A | 7/1998 | Lopez et al. |
| 5,810,781 A | 9/1998 | Bierman |
| 5,851,197 A | 12/1998 | Marano et al. |
| 5,858,005 A | 1/1999 | Kriesel |
| 5,954,643 A | 9/1999 | VanAntwerp et al. |
| 5,954,708 A | 9/1999 | Lopez et al. |
| 5,968,001 A | 10/1999 | Freeman |
| 5,968,011 A | 10/1999 | Larsen et al. |
| 5,971,950 A | 10/1999 | Lopez et al. |
| 5,980,506 A | 11/1999 | Mathiasen |
| 5,989,240 A | 11/1999 | Strowe |
| 6,017,328 A | 1/2000 | Fischell et al. |
| D422,356 S | 4/2000 | Marano et al. |
| 6,056,718 A | 5/2000 | Funderburk et al. |
| D427,308 S | 6/2000 | Zinger |
| 6,074,371 A | 6/2000 | Fischell |
| 6,077,259 A | 6/2000 | Caizza et al. |
| 6,086,575 A | 7/2000 | Meislov |
| 6,090,068 A * | 7/2000 | Chanut .................... 604/93.01 |
| 6,093,172 A | 7/2000 | Funderburk et al. |
| 6,093,182 A | 7/2000 | Lampropoulos et al. |
| 6,093,183 A | 7/2000 | Pavkovich |
| 6,109,259 A | 8/2000 | Fitzgerald |
| 6,123,690 A | 9/2000 | Meislov |
| 6,132,418 A | 10/2000 | Lassal et al. |
| 6,142,446 A | 11/2000 | Leinsing |
| 6,152,913 A | 11/2000 | Feith et al. |
| 6,165,168 A | 12/2000 | Russo |
| 6,192,568 B1 | 2/2001 | Kafrawy et al. |
| 6,213,996 B1 | 4/2001 | Jepson et al. |
| D445,501 S | 7/2001 | Niedospial, Jr. |
| 6,290,688 B1 | 9/2001 | Lopez et al. |
| 6,293,925 B1 | 9/2001 | Safabash et al. |
| 6,302,866 B1 | 10/2001 | Marggi |
| 6,355,021 B1 | 3/2002 | Nielsen et al. |
| 6,371,943 B1 | 4/2002 | Racz et al. |
| 6,461,329 B1 | 10/2002 | Van Antwerp et al. |
| 6,475,196 B1 | 11/2002 | Vachon |
| 6,488,663 B1 | 12/2002 | Steg |
| 6,517,517 B1 | 2/2003 | Farrugia et al. |
| 6,520,938 B1 | 2/2003 | Funderburk et al. |
| 6,529,776 B1 | 3/2003 | Leonard et al. |
| 6,572,586 B1 | 6/2003 | Wojcik |
| 6,579,267 B2 | 6/2003 | Lynch et al. |
| 6,607,509 B2 | 8/2003 | Bobroff et al. |
| 6,629,949 B1 | 10/2003 | Douglas |
| 6,659,982 B2 | 12/2003 | Douglas et al. |
| 6,685,674 B2 | 2/2004 | Douglas et al. |
| 6,736,797 B1 | 5/2004 | Larsen et al. |
| 6,749,589 B1 | 6/2004 | Douglas et al. |
| 6,830,562 B2 | 12/2004 | Mogensen et al. |
| 6,877,713 B1 | 4/2005 | Gray et al. |
| 6,878,137 B2 | 4/2005 | Benchetrit |
| 6,923,791 B2 | 8/2005 | Douglas |
| 6,949,084 B2 | 9/2005 | Marggi et al. |
| 6,997,907 B2 | 2/2006 | Safabash et al. |
| 7,052,483 B2 | 5/2006 | Wojcik |
| 7,147,623 B2 | 12/2006 | Mathiasen |
| 7,207,974 B2 | 4/2007 | Safabash et al. |
| 7,211,068 B2 | 5/2007 | Douglas |
| 7,297,138 B2 | 11/2007 | Fangrow, Jr. |
| 7,300,419 B2 | 11/2007 | Fangrow, Jr. |
| 7,309,326 B2 | 12/2007 | Fangrow, Jr. |
| 7,311,694 B2 | 12/2007 | Fangrow, Jr. |
| 7,314,463 B2 | 1/2008 | Fangrow, Jr. |
| 7,331,939 B2 | 2/2008 | Fangrow, Jr. |
| 7,407,491 B2 | 8/2008 | Fangrow, Jr. |
| 7,628,776 B2 | 12/2009 | Gibson et al. |
| 2001/0003149 A1 | 6/2001 | Utterberg et al. |
| 2001/0009988 A1 | 7/2001 | Kafrawy et al. |
| 2001/0049519 A1 | 12/2001 | Holman et al. |
| 2002/0045867 A1 | 4/2002 | Nielsen et al. |
| 2002/0065484 A1 | 5/2002 | Douglas et al. |
| 2002/0095138 A1 | 7/2002 | Lynch et al. |
| 2002/0120231 A1 | 8/2002 | Douglas et al. |
| 2002/0123740 A1 | 9/2002 | Flaherty et al. |
| 2002/0161332 A1 | 10/2002 | Ramey |
| 2002/0173769 A1 | 11/2002 | Gray et al. |
| 2003/0060781 A1 | 3/2003 | Mogensen et al. |
| 2003/0109829 A1 | 6/2003 | Mogensen et al. |
| 2003/0125669 A1 | 7/2003 | Safabash et al. |
| 2003/0130619 A1 | 7/2003 | Safabash et al. |
| 2003/0158520 A1 | 8/2003 | Safabash et al. |

| | | | | | |
|---|---|---|---|---|---|
| 2003/0176852 A1 | 9/2003 | Lynch et al. | EP | 0864333 | 9/1998 |
| 2003/0199823 A1 | 10/2003 | Bobroff et al. | WO | WO 88/03816 | 6/1988 |
| 2003/0225373 A1 | 12/2003 | Bobroff et al. | WO | WO 97/37713 | 10/1997 |
| 2004/0002682 A1 | 1/2004 | Kovelman et al. | WO | WO 88/03816 | 6/1998 |
| 2004/0044306 A1 | 3/2004 | Lynch et al. | WO | WO 98/41384 | 9/1998 |
| 2004/0138620 A1 | 7/2004 | Douglas et al. | WO | WO 98/58693 | 12/1998 |
| 2004/0143216 A1 | 7/2004 | Douglas et al. | WO | WO 99/33504 | 7/1999 |
| 2004/0143241 A1 | 7/2004 | Douglas et al. | WO | WO 99/44655 | 9/1999 |
| 2004/0158207 A1 | 8/2004 | Hunn et al. | WO | WO 00/25852 | 5/2000 |
| 2004/0204687 A1 | 10/2004 | Mogensen et al. | WO | WO 00/35530 | 6/2000 |
| 2005/0035014 A1 | 2/2005 | Cane | WO | WO 01/52617 | 1/2001 |
| 2005/0043687 A1 | 2/2005 | Mogensen et al. | WO | WO 01/62330 | 8/2001 |
| 2005/0124936 A1 | 6/2005 | Mogensen et al. | WO | WO 01/76684 | 10/2001 |
| 2005/0277887 A1 | 12/2005 | Douglas et al. | WO | WO 01/85233 | 11/2001 |
| 2006/0129123 A1 | 6/2006 | Wojcik | WO | WO 02/068014 | 9/2002 |
| 2007/0049870 A1 | 3/2007 | Gray et al. | WO | WO 02/070037 | 9/2002 |
| 2007/0185441 A1 | 8/2007 | Fangrow, Jr. | WO | WO 02/081012 | 10/2002 |
| 2007/0185454 A1 | 8/2007 | Fangrow, Jr. | WO | WO 02/083206 | 10/2002 |
| 2007/0185455 A1 | 8/2007 | Fangrow, Jr. | WO | WO 02/094352 | 11/2002 |
| 2007/0213673 A1 | 9/2007 | Douglas | WO | WO 02/100457 | 12/2002 |
| | | | WO | WO 03/022348 | 3/2003 |
| | | | WO | WO 03/026728 | 4/2003 |
| | | | WO | WO 03/068305 | 8/2003 |

FOREIGN PATENT DOCUMENTS

| | | |
|---|---|---|
| EP | 0256694 | 2/1988 |
| EP | 0268480 | 5/1988 |
| EP | 0363953 | 4/1990 |
| EP | 0268480 | 10/1990 |
| EP | 0451040 | 10/1991 |
| EP | 0363953 | 12/1994 |
| EP | 0319764 | 8/1995 |

OTHER PUBLICATIONS

Medtronic Minimed—History; htt://www.minimed.com/about/history.html; Jun. 5, 2006.

* cited by examiner

INFUSION HUB ASSEMBLY AND FLUID LINE DISCONNECT SYSTEM

RELATED APPLICATION

This application is a continuation of U.S. application Ser. No. 10/744,862, filed 22 Dec. 2003, now abandoned, which is a continuation of U.S. application Ser. No. 10/091,123, filed 4 Mar. 2002 and is now U.S. Pat. No. 6,685,674, which claims the benefit of U.S. provisional application Ser. No. 60/299,842 filed 19 Jun. 2001 and U.S. provisional application Ser. No. 60/273,490 filed 4 Mar. 2001. The preceding applications are incorporated herein by reference.

SUMMARY OF THE INVENTION

In various embodiments, the present invention provides an infusion hub assembly, comprising: a wing having a hole passing therethrough; a hub received in the hole in the wing, the hub having a bore passing therethrough, with an upper portion of the circular hub having an attachment surface thereon; an infusion cannula extending downwardly away from the wing, the infusion cannula being in fluid communication with the bore passing through the hub; a cover having a bore passing therethrough with an inner attachment surface adapted to mate with the attachment surface on the upper portion of the hub; and a septum positioned in alignment with the bore passing through the cover.

In various embodiments, the upper portion of the hub is circular and has an attachment surface extending circumferentially therearound. In various embodiments, this attachment surface comprises a lip extending circumferentially therearound.

The present infusion hub assembly comprises a cover having a bore through which an insertion needle is positioned when initially positioning the wing of the assembly on a patient's skin with the infusion cannula extending subcutaneously. In various embodiments, the cover holds a septum therein to advantageously seal the pathway into the patient (when the insertion needle is not piercing therethrough).

In various embodiments, the cover is dimensioned to be snap-fit over the infusion hub. In various embodiments, the cover has a central bore through which the insertion needle passes when the assembly is positioned subcutaneously.

Thereafter, the novel rotatable infusion housing is attached onto the top of the cover. In various embodiments, the rotatable housing has an attachment surface adapted to mate with an outer attachment surface on the upper portion of the cover. Thus, in various embodiments, the rotatable housing is also dimensioned to be snap-fit over the cover, which is in turn snap-fit over the infusion hub.

In various aspects, the attachment surface on both the cover and the rotatable housing comprises a recess extending circumferentially therearound. These recesses mate with lips extending from an upper portion of the infusion hub and the cover, respectively. In various aspects, the infusion hub and the rotatable housing are circular such that the rotatable housing can turn freely, while still providing continuous infusion of medication (or other desired fluid substances) subcutaneously into the patient.

In various embodiments, the rotatable housing comprises a curved needle or housing cannula passing at least partially through a radial bore in the rotatable housing, wherein a first end of the curved needle is positioned to extend downwardly into the bores in the cover and the hub when the rotatable housing is attached to the cover. Additionally, an infusion tube is received into the radial bore of the rotatable housing in fluid communication with the curved needle.

Advantages of having a rotatable infusion housing which can turn freely, while still providing continuous infusion subcutaneously into the patient include: (i) avoiding kinks in the infusion tube, and (ii) avoiding having to tape the infusion housing to the patient, thus (iii) permitting the patient to position an infusion pump (which feeds fluid into the infusion tube) at different locations one the patient's body.

In another aspect of the invention, the present invention provides an infusion connector set comprising: a proximal connector; a septum received in the proximal connector; a distal connector; a septum received in the distal connector; and a flanged needle which penetrates both the septums in the proximal and distal connectors when the proximal and distal connectors are connected together.

It is to be understood, however, that reference made herein to a "proximal" and "distal" connector is only exemplary. Thus, the flanged needle may instead move to various positions within the distal connector rather than within the proximal connector. Accordingly, the present invention refers to a "first" and a "second" connector. In various embodiments, the "first" connector is the "proximal" connector and the "second" connector is the "distal" connector. In alternate embodiments, the connectors are reversed such that the "first" connector is the "distal" connector and the "second" connector is the "proximal" connector.

In various embodiments, the flanged needle is slidably movable within a slot in the distal connector. In various aspects, the flanged needle may be moved to a position at which the needle does not penetrate the proximal septum in the proximal connector, yet is still held within the proximal connector.

Thus, when the proximal and distal connectors are fastened together, the needle provides a fluid path therethrough. When the distal connectors is uncoupled from the proximal connector, the septum in the distal connector will seal (since the flanged needle is held within the proximal connector, and thus is no longer in contact with the septum in the distal connector).

In various embodiments, the flange of the flanged needle protrudes through the slot in the distal connector such that an operator may grab onto the flange and move the flanged needle along in the slot in the distal connector. Thus, the flanged needle may conveniently be moved to a position in which the needle no longer penetrates the septum in the proximal connector. Thus, the septum in the proximal connector will seal itself, preventing contamination or exposure to the substance being delivered through the infusion tubing.

An advantage of having the proximal and distal connector easily disconnectable from one another (with their respective septums sealing the fluid path through both connectors) is that it facilitates switching between different infusion lines.

A further advantage of providing the distal connector with its own septum is that a patient can manually disconnect the proximal and distal connectors and then inject a syringe (containing an alternate medication or substance) through the septum in the distal connector, and into the patient.

In various embodiments, the infusion connector set further comprises a retainer mounted at the distal end of the proximal connector. In various embodiments, this retainer closes the distal end of the slot in the proximal connector, such that movement of the flanged needle is retained to back and forth movement within the proximal connector.

In various embodiments, the proximal and distal connectors are dimensioned such that one connector may be inserted into the other, and then rotated into an interlocked position.

This may be achieved by providing one of the connectors with at least one tab extending therefrom, and the other of the connectors with at least one recess therein. The at least one recess is dimensioned to receive the at least one tab therein when the proximal and distal connectors are connected together. In various embodiments, the connector comprising the at least one tab is the proximal connector, and the connector comprising the at least one slot is the distal connector.

Still other features and advantages of the present invention will become apparent to those skilled in the art from a reading of the following detailed description of embodiments constructed in accordance therewith, taken in conjunction with the accompanying drawings.

DETAILED DESCRIPTION OF THE DRAWINGS

FIGS. 1 to 6 illustrate an infusion hub assembly according to the present invention. FIGS. 7 to 15 illustrate an infusion connector set according to the present invention.

Referring first to FIGS. 1 to 6, an infusion hub assembly 10 is provided. A large wing or patch 12 having a hole 13 passing therethrough is provided. Wing 12 is positioned on the surface of a patient's skin. In various embodiments, the underside of wing 12 has an adhesive surface, securing it to a patient's skin. In alternate embodiments, the wing 12 is instead taped directly onto the patient's skin.

Figure 1:
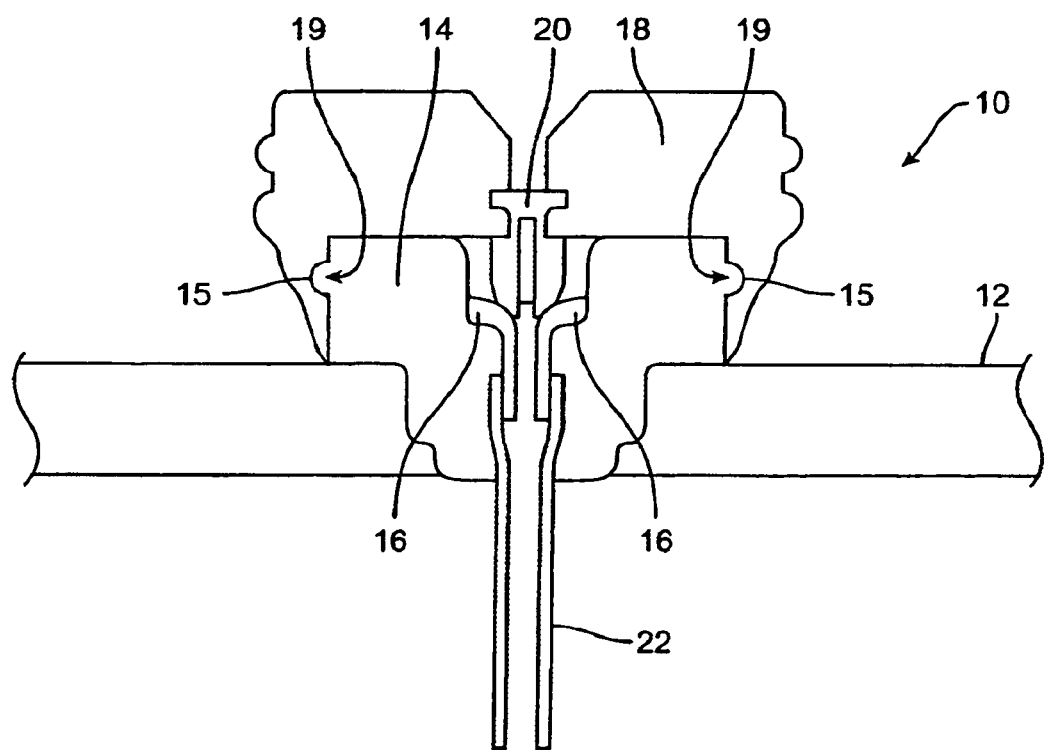
FIG. 1 is a sectional side elevation view of an infusion hub assembly according to the present invention.

As shown in FIG. 1, assembly 10 comprises wing 12, hub or housing 14 and cover 18. In various aspects, all, or at least the upper portion of hub 14 is circular. Hub 14 is received into a circular shaped hole 13 in wing 12. In various embodiments, hole 13 is stepped in diameter, and circular hub 14 also has a stepped diameter such that hub 14 fits into hole 13, as shown. Circular hub 14 has a central bore passing vertically therethrough. A needle guide 16 is positioned within this bore through circular hub 14 as also shown. Needle guide 16 may be funnel-shaped, and may be made of metal.

In various aspects, an upper portion of circular hub 14 has an attachment surface onto which cover 18 can be snap fit. For example, various aspects, circular hub 14 has a lip 15 extending at least partially circumferentially therearound. In various embodiments, cover 18 has an interior groove 19 extending at least partially circumferentially therearound. In various embodiments, as well, cover 18 is made of a flexible material such that it can be easily snap-fit over the upper portion of circular hub 14.

As can also be seen, a septum 20 is also provided. Septum 20 may be held by cover 18 (such that when cover 18 is removed from hub 14, septum 20 is also removed). As can also be seen, septum 20 may be positioned such that it is received within needle guide 16 when cover 18 is positioned over infusion housing 14. Septum 20 may be made from a plug of self-sealing elastomeric material.

A infusion cannula 22 extends downwardly from wing 12. Thus, infusion cannula 22 is positioned subcutaneously when wing 12 rests on the patient's skin. Infusion cannula 22 is thus used for subcutaneously infusing medication into the patient. In various embodiments, the proximal end of infusion cannula 22 may be positioned to be received within the lower portion of circular hub 14, and may also be received around an end of needle guide 16, as shown, however, the present invention is not so limited. Many other systems for attaching infusion cannula 16 such that it extends downwardly from wing 12 are also contemplated within the scope of the present invention.

Figure 2:
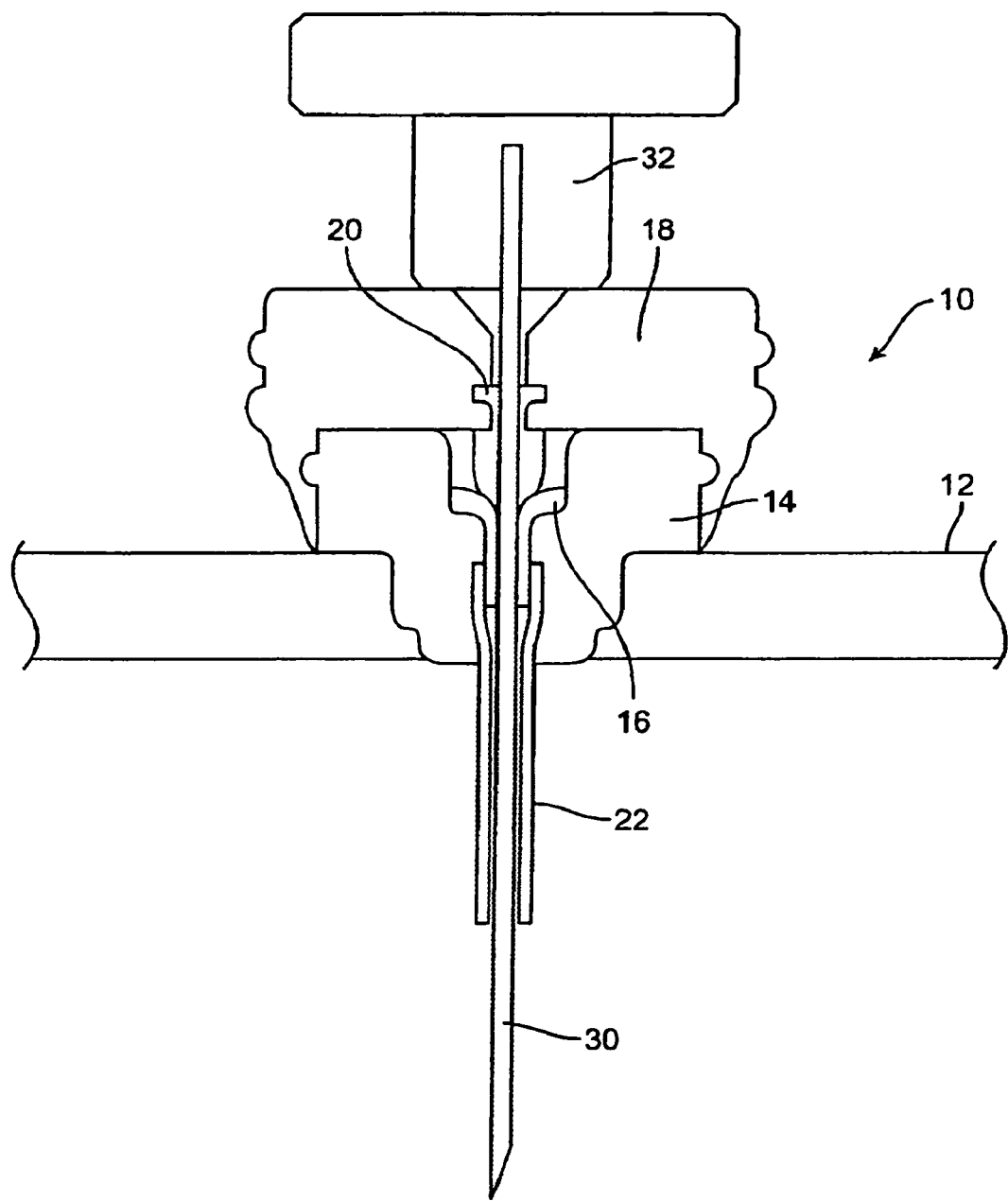
FIG. 2 is a sectional side elevation view similar to FIG. 1, but with an insertion needle passing therethrough.

Referring next to FIG. 2, a various system for positioning assembly 10 such that infusion cannula 22 is positioned subcutaneously is also provided. Specifically, an insertion needle 30, (which is supported by a handle 32) is inserted through the central bores of protective cover 18 and circular hub 14. Thus, needle 30 passes through septum 20, and extends downwardly, passing out the bottom distal end of infusion cannula 22. When needle 30 is inserted through infusion cannula 22, as shown in FIG. 2, the operator simply applies pressure downwardly onto handle 32 such that wing 12 is pushed down into contact with the patient's skin and infusion cannula 22 is subcutaneously inserted.

After assembly 10 has been positioned with its wing 12 resting against the patient's skin, and with infusion cannula 22 positioned subcutaneously, (i.e.: as shown in FIG. 2), the operator then simply removes needle 30 by pulling upwardly on handle 32. When needle 30 is initially removed, septum 20 will self-seal, ensuring no contamination enters from the atmosphere through cannula 22 and thus into the subcutaneous pathway under the patient's skin.

After needle 30 is removed, it is replaced by rotatable infusion housing 40, as follows.

Figure 3:
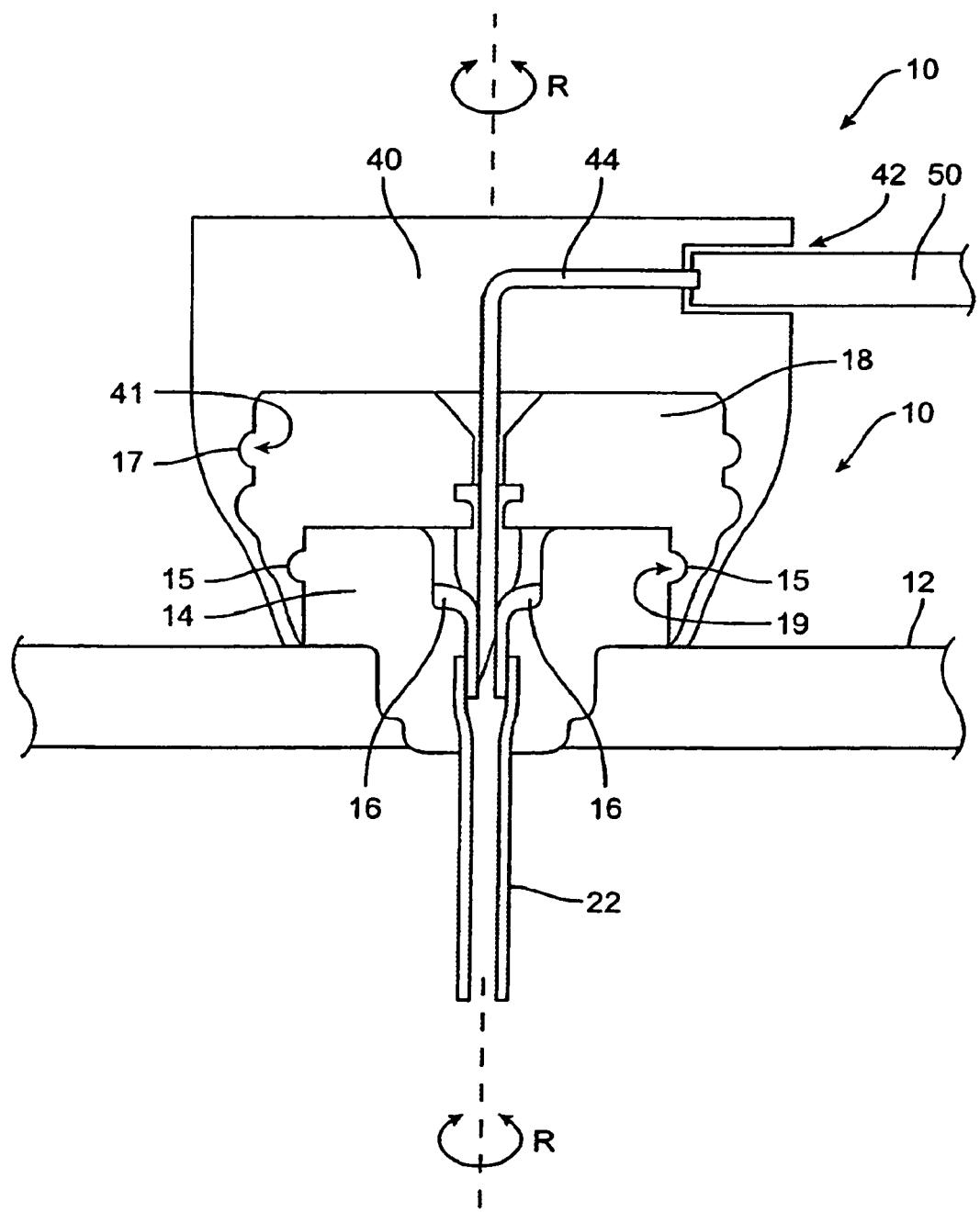
FIG. 3 is a sectional side elevation view similar to FIGS. 1 and 2, but with the insertion needle removed, and replaced by a rotatable infusion housing.

As shown in FIG. 3, rotatable housing 40 is then attached over cover 18. Rotatable housing 40 may be made of a flexible material such that it can be snap-fit over cover 18 (similar to how cover 18 fits over hub 14). Specifically, rotatable housing 40 may also have an inner attachment surface such as an interior grooves 41 which extend at least partially circumferentially therearound.

Figure 4:
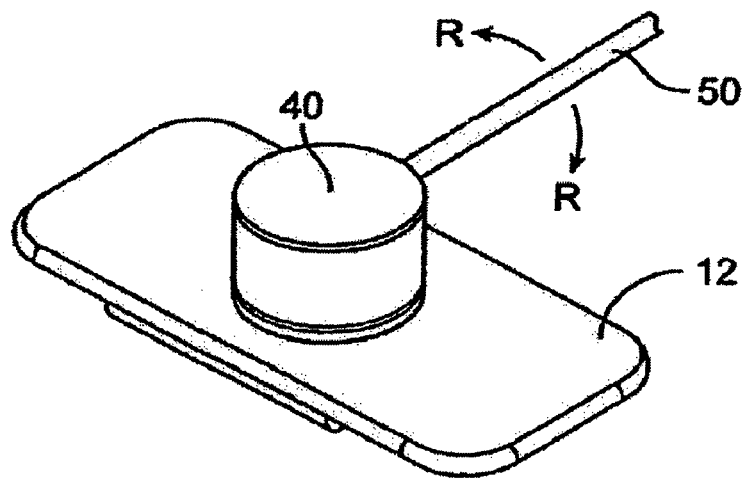
FIG. 4 is a perspective view of the assembled infusion hub assembly.
Figure 5:
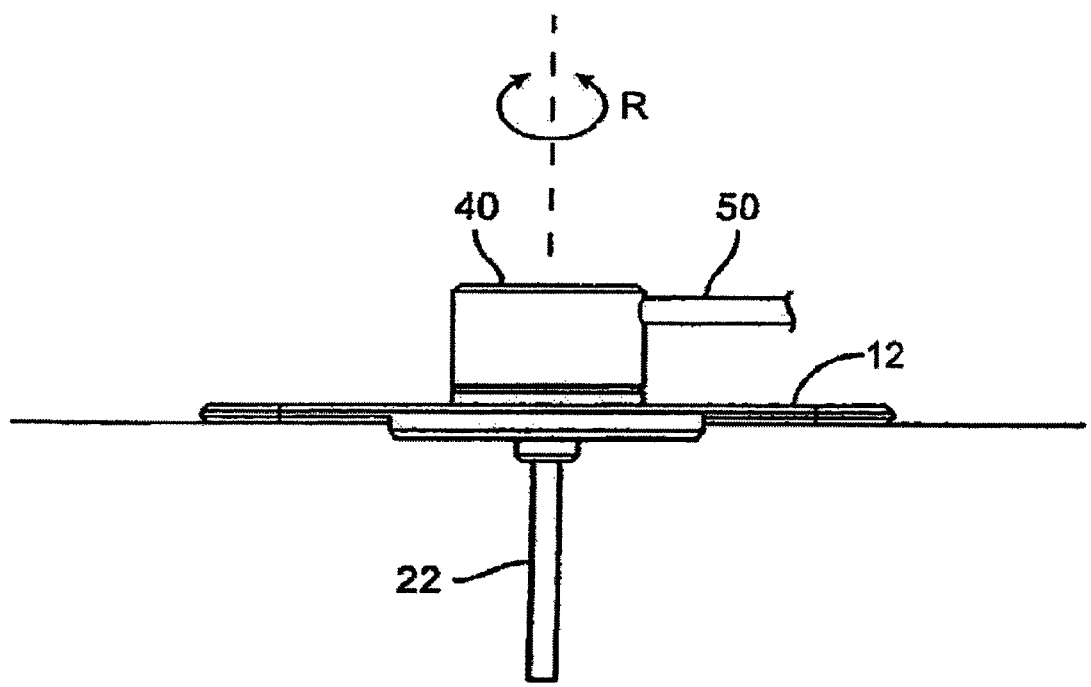
FIG. 5 is a side elevation view of the assembled infusion hub assembly.

An advantage of interior grooves 41 extending at least partially circumferentially around lip 17 of cover 18 is that housing 40 is therefore rotatable with respect to circular hub or housing 14. Thus, as shown in FIGS. 4 and 5, housing 40 may freely be rotated in direction R.

Referring back to FIG. 3, an infusion tube 50 may be used to deliver medication (or any other desired substance) subcutaneously to the patient. Tube 50 may be received into a radially extending bore 42 in housing 40. A curved needle or housing cannula 44 may be attached to the end of tube 50, and is positioned such that its downwardly facing distal end is received directly into needle guide 16 in the bore of circular housing 14. Since the distal end of curved needle 44 points downwardly from the center of rotatable housing 40, and is positioned in the central bores passing through cover 18 and circular housing 14, housing 40 is free to rotate in direction R about its central axis while medication or any other desired substance is infused through tube 50.

Figure 6:
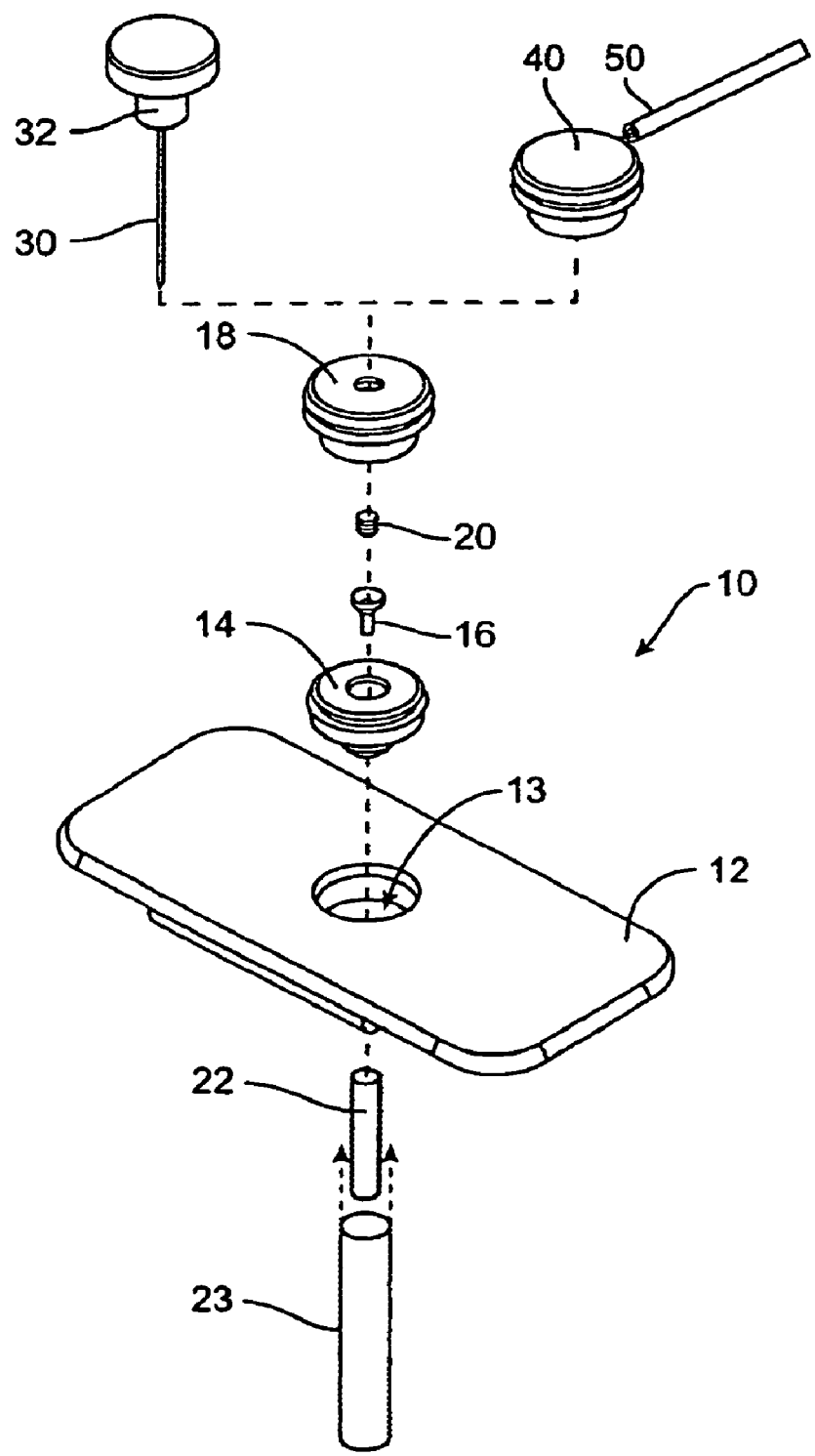
FIG. 6 is an exploded perspective view of the present infusion hub assembly, showing alternate positioning of the insertion needle passing through the cover and of the rotatable infusion housing fit over the cover.

FIG. 6 shows an exploded view of the present system in which either: (i) the introducing needle 30 or, (ii) the rotatable housing 40 and infusion tube 50 are attached to cover 18 and pass through septum 20, into circular housing 14. As can also be seen, in various embodiments, an optional removable protective cylinder 23 can be received over infusion cannula 22, to protect the cannula and keep the cannula free of contamination prior to its use.

Turning now to FIGS. 7 to 15, an infusion connector set is also provided. In various aspects, connector assembly 100 comprises a proximal connector 110 and a distal connector 120. It is to be understood that connector 110 could instead be the distal connector and connector 120 could instead be the proximal connector, according to the user's preferences.) As illustrated herein, assembly 100 is used to provide a detachable coupling link mid-way along infusion tube 50. It is to be understood, however, that while connector assembly 100 (FIGS. 7 to 15) may be used in conjunction with the infusion hub assembly 10 (FIGS. 1 to 6), it need not be. Rather, each of connector assembly 100 and infusion hub assembly 10 may be used separately. Thus, the tube numbered "50" in FIGS. 1 to 6 may, or may not, be the same or different from the tubes numbered "50" in FIGS. 7 to 15.

Figure 7:
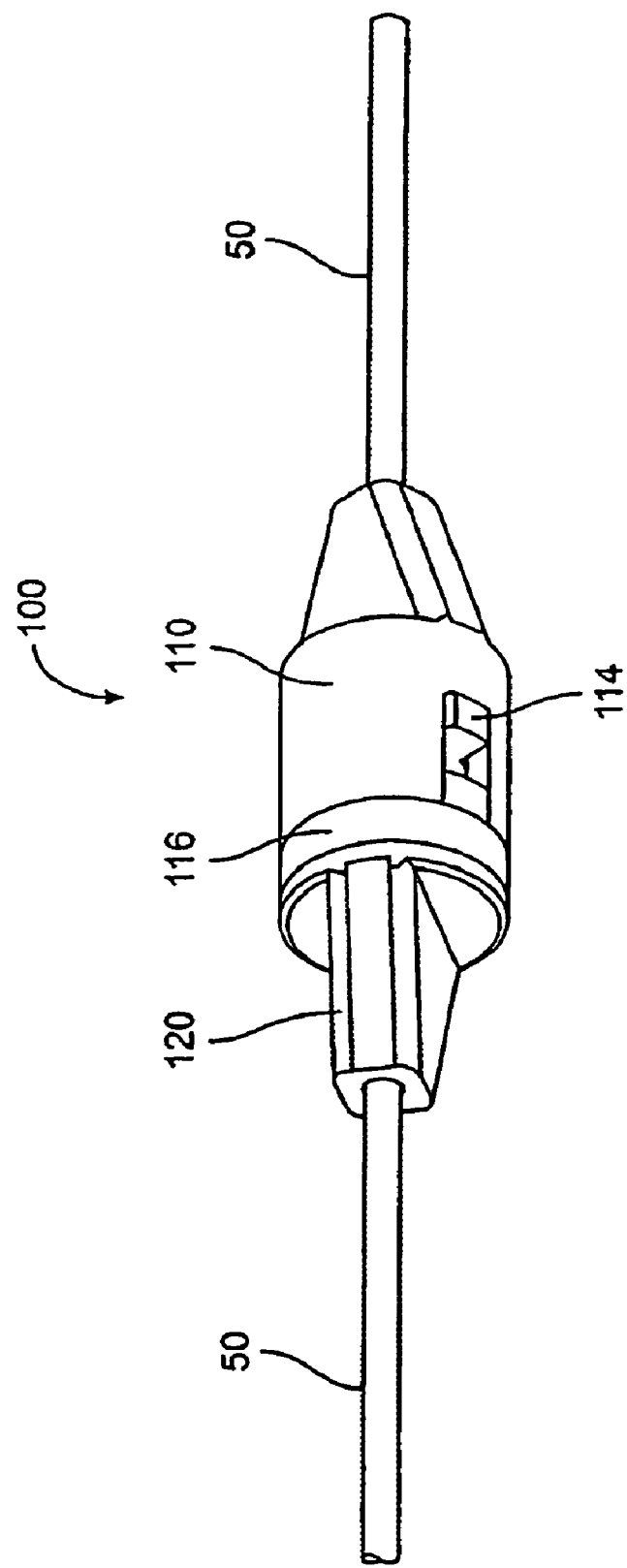
FIG. 7 is a perspective view of an infusion connector set according to the present invention.
Figure 8:
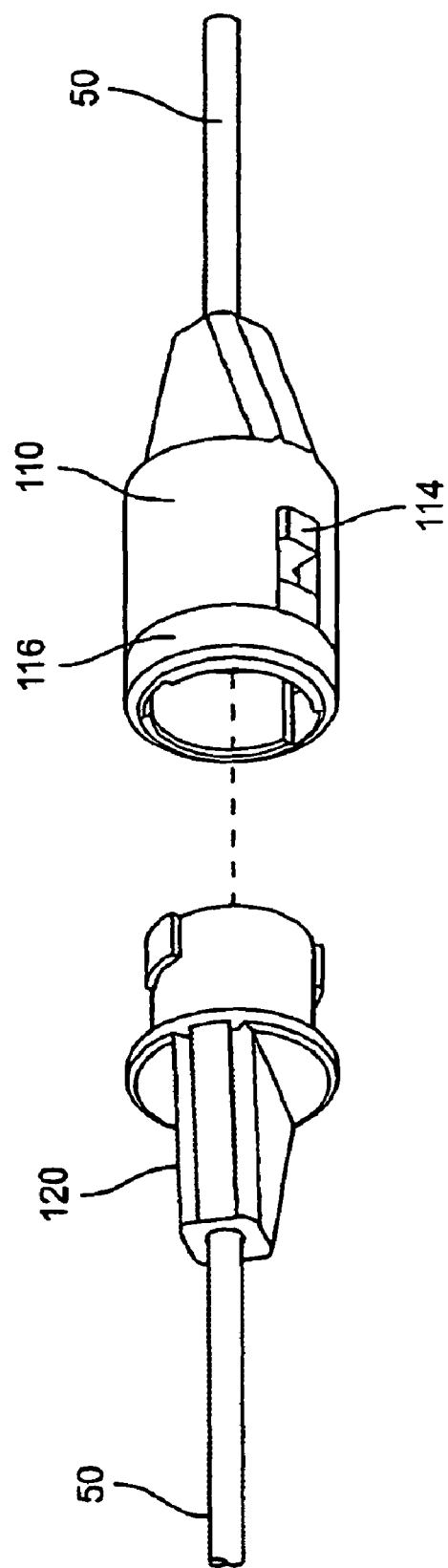
FIG. 8 is a perspective view similar to FIG. 7, showing the proximal and distal connector disconnected from one another.

FIG. 7 shows proximal connector 120 and distal connector 110 coupled together. FIG. 8 shows proximal connector 120 and distal connector 110 uncoupled from one another. As will be explained, the present connector set provides a system in which, when the proximal and distal connectors are fastened together, fluid flows freely through the assembly. When the proximal and distal connectors are no longer fastened or coupled together, the present invention provides a novel self-sealing system which prevents contamination from entering the flow path through either of the proximal or distal connectors. Specifically, as will be explained, a self-sealing septum is positioned in each of the proximal and distal connectors. Also, the proximal connector supports a flanged needle assembly which can be moved such that a septum in the proximal needle self-seals as desired.

Figure 10:
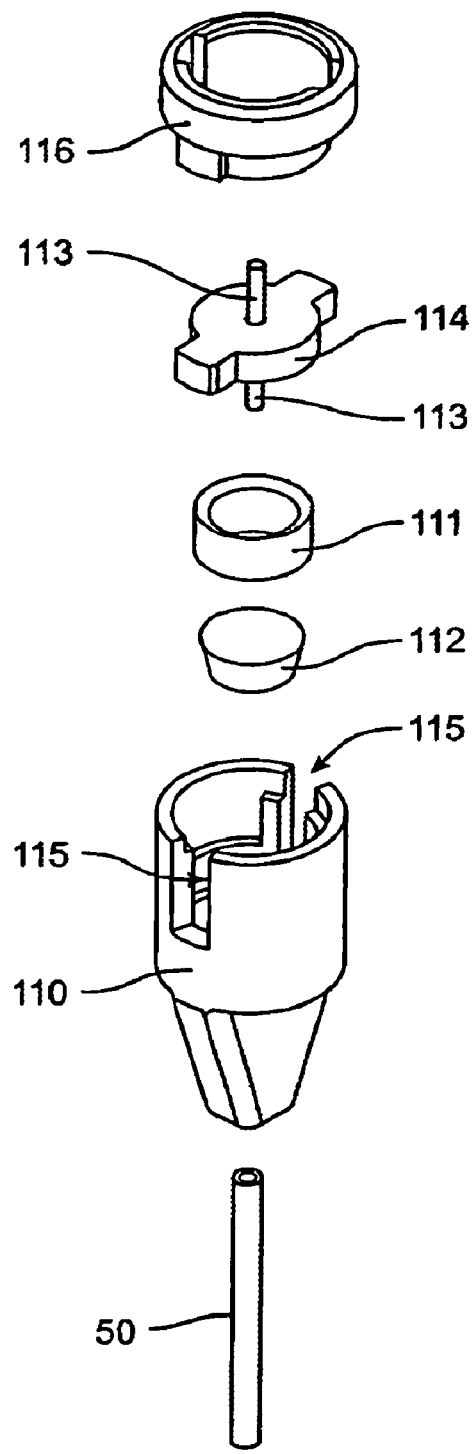
FIG. 10 is an exploded perspective view of the proximal connector assembly.

Referring to FIG. 10, proximal connector 110 has a septum housing 111 received therein. A self-sealing septum 112 is held in position by septum housing 111. A flanged needle assembly comprising a flange 114 and a needle 113 is then received therein. As will be explained, flange 114 can be moved up and down in slots 115 in proximal connector 110 (thereby moving needle 113 to different positions). A retainer 116 is then received over flanged needle assembly 113/114.

Retainer 116 prevents flange 114 from escaping from slot 115. Thus, needle 113 remains supported within proximal connector 110 at all times.

Figure 11:
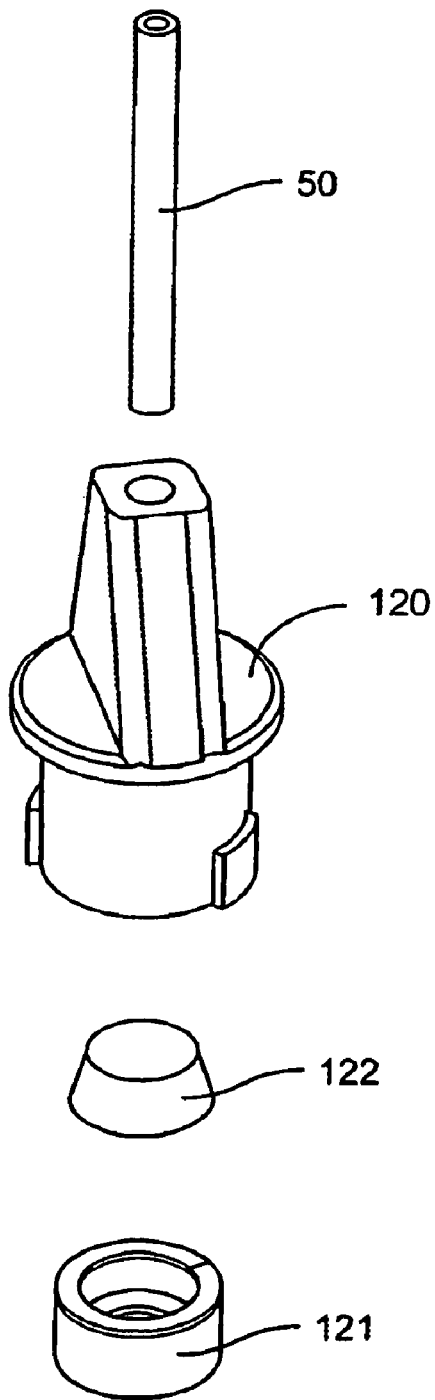
FIG. 11 is an exploded perspective view of the distal connector assembly.
Figure 12:
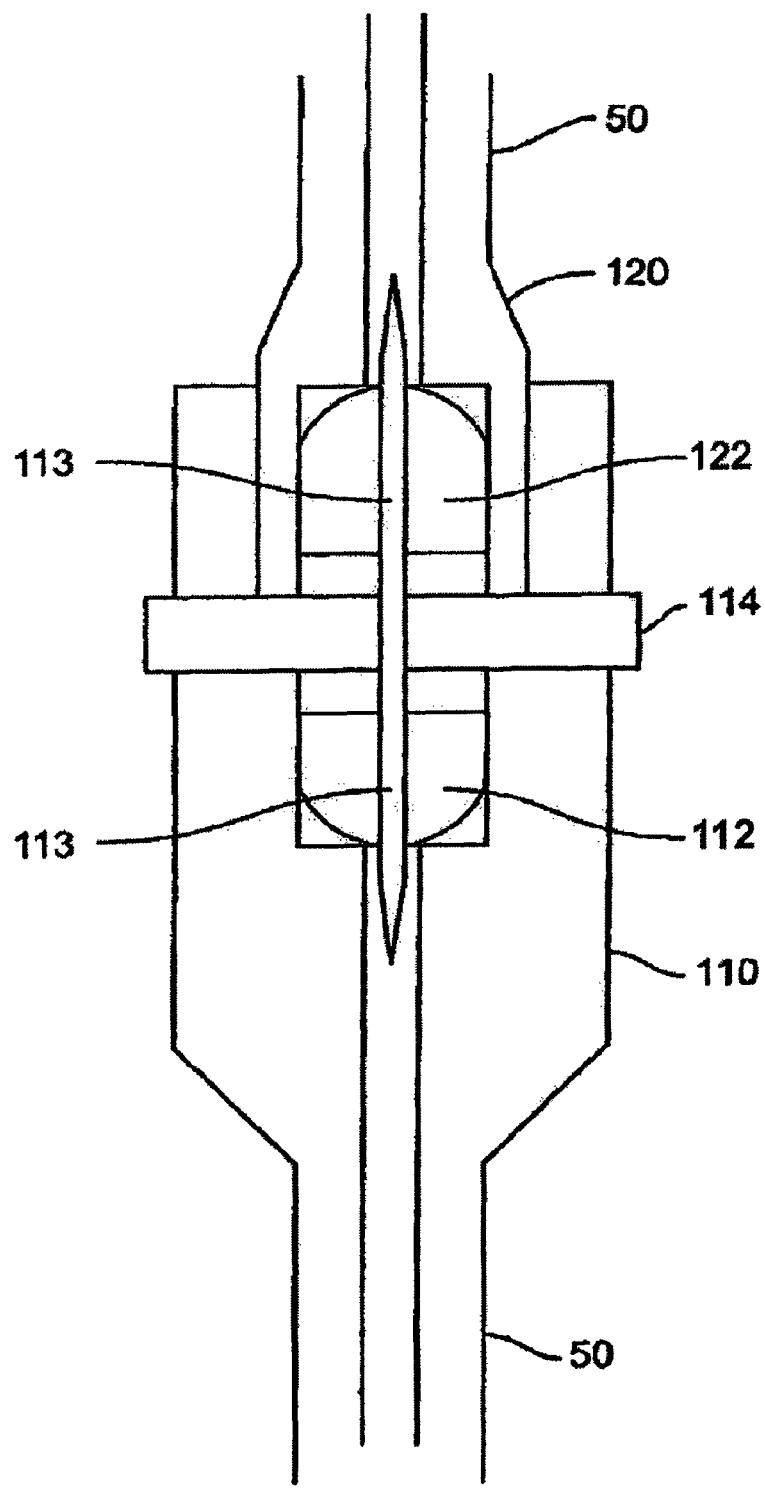
FIG. 12 is a schematic sectional view corresponding to FIG. 7. (Corresponding to a view taken along line 12-12 in FIG. 13).
Figure 13:
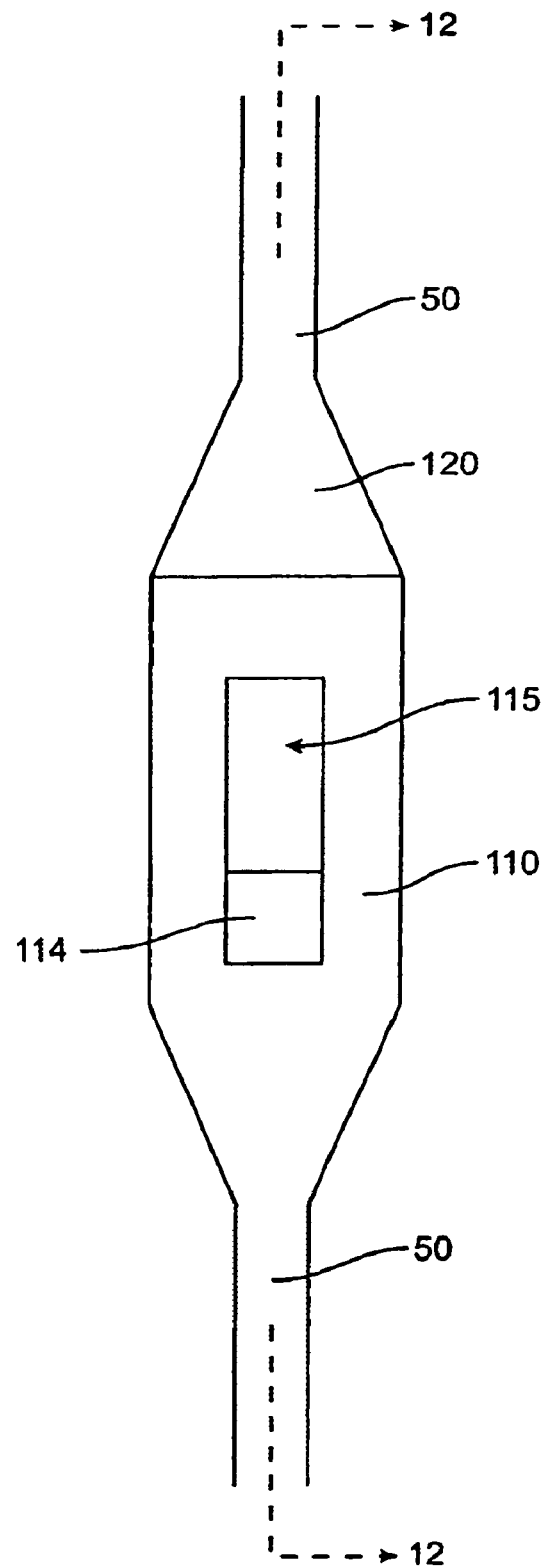
FIG. 13 is a side elevation view corresponding to FIG. 12 (showing the slot in which the flange supporting the flanged needle moves).
Figure 14:
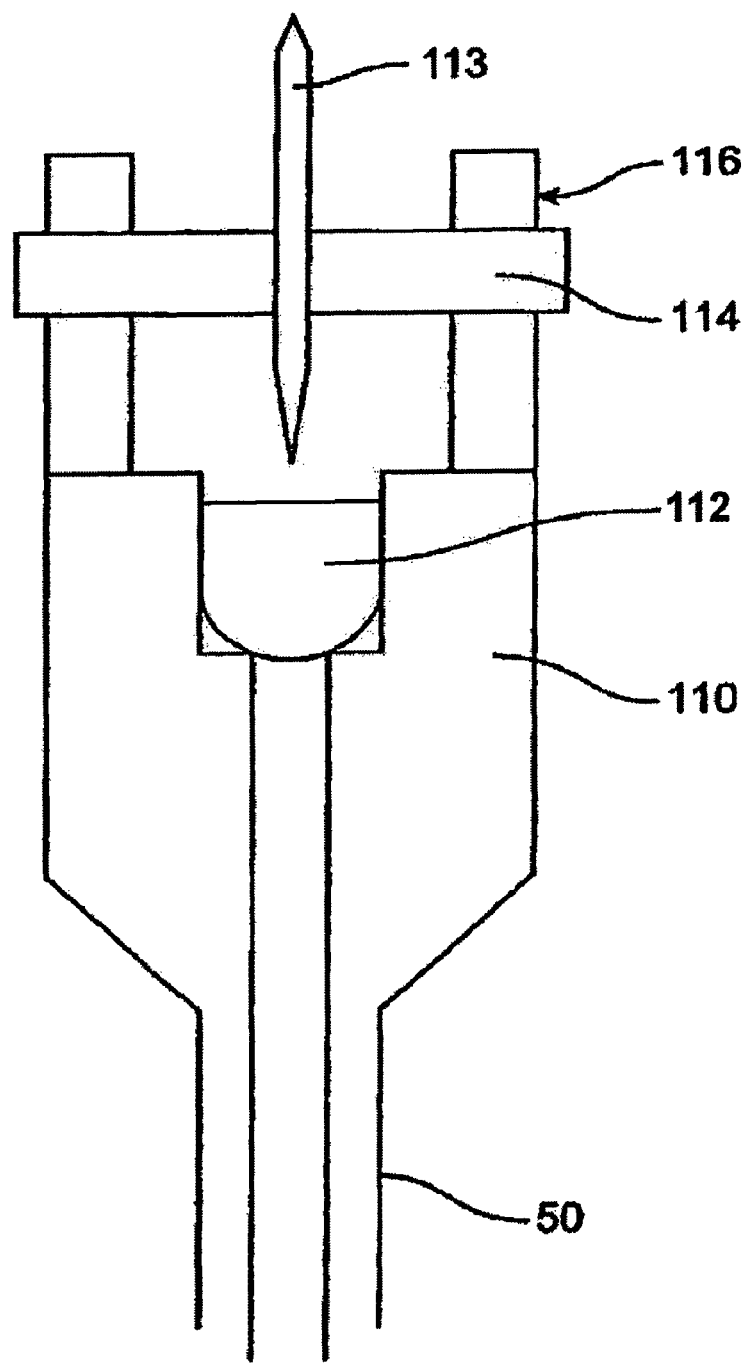
FIG. 14 is a schematic sectional view of the proximal connector of the system of FIG. 12, after the distal connector has been uncoupled and removed and the flanged needle has been moved in the slot such that it does not penetrate the septum in the proximal connector. (Corresponding to a view taken along line 14-14 in FIG. 15).
Figure 15:
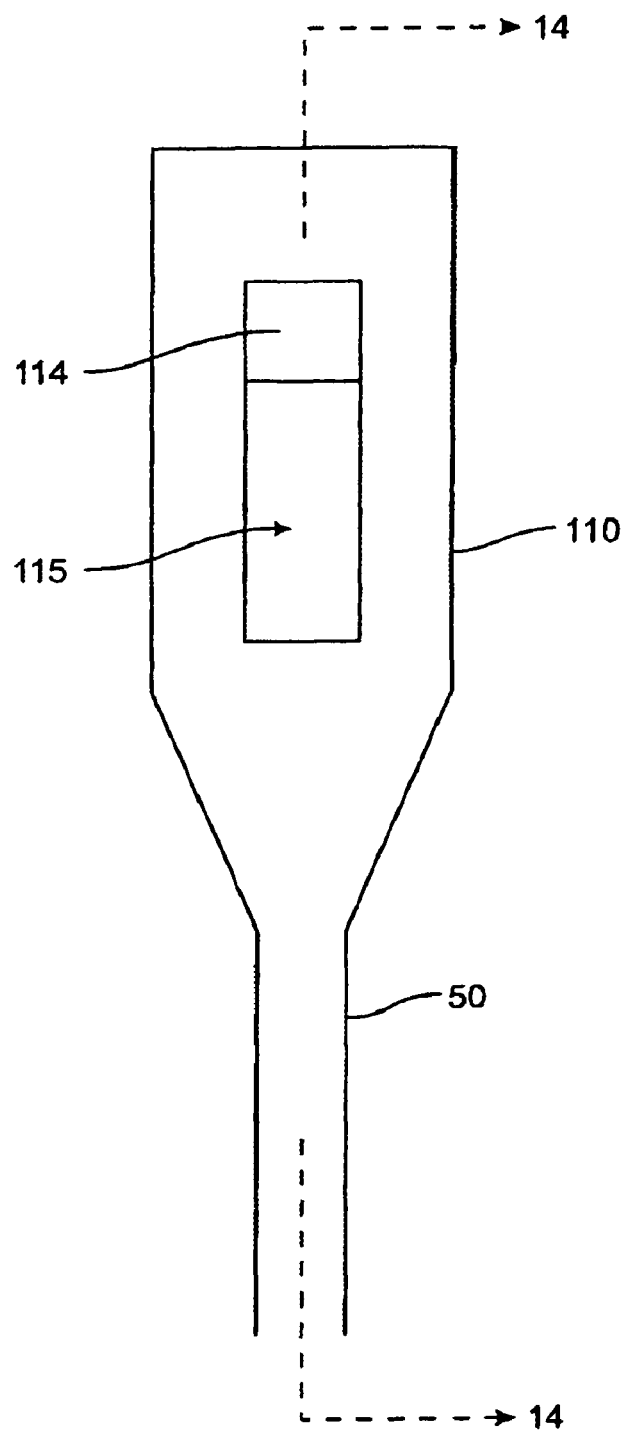
FIG. 15 is a side elevation view corresponding to FIG. 14.

Referring to FIG. 11, distal connector 120 has a septum housing 121 received therein. A self-sealing septum 122 is held in position by septum housing 121.

When assembled together, as shown in FIG. 7 (and as illustrated schematically in FIGS. 12 and 13), needle 113 penetrates both of septums 112 and 122, permitting flow through tubes 50.

When the connectors are disconnected from one another, (i.e.: when distal connector 120 is detached from proximal connector 110) needle 113 (which is held within proximal connector 110) will no longer penetrate distal septum 122 in distal connector 120. Thus, distal septum 122 will self-seal, such that the subcutaneous pathway into the patient (i.e.: the path through distal connector 120, tube 50 and rotatable housing 40 into the patient) will be sealed. However, should a user so desire, a separate syringe injection needle may be inserted through distal septum 122 in distal connector 120 such that different or additional medication (or other substances) can be subcutaneously introduced into the patient.

Figure 9:
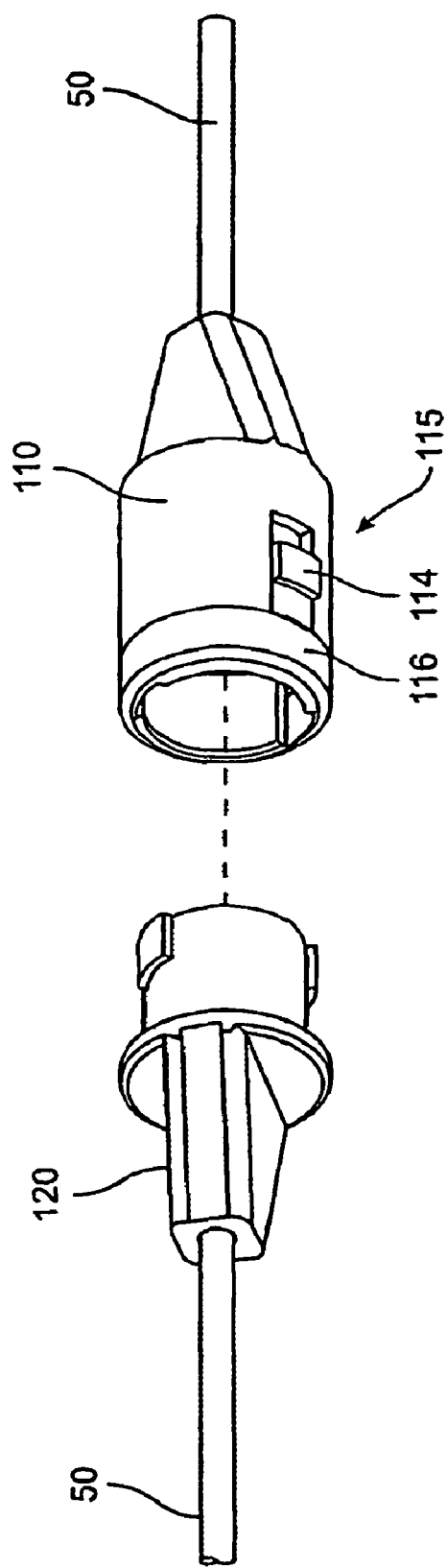
FIG. 9 is a view similar to FIG. 8, but with the flanged needle moved such that it does not penetrate the proximal septum.

In accordance with the present invention, a novel system of sealing proximal septum 112 in proximal connector 110 is also provided. Referring to FIG. 9 (and to schematic FIGS. 14 and 15), flange 114 is moved distally along slot 115 such that it carries needle 113 to a position at which it no longer penetrates proximal septum 112.

In various embodiments, flange 114 protrudes slightly through slots 115 on opposite sides of proximal connector 110, to permit an operator to grasp onto flange 114 and slide it into a position against retainer 116 (such that needle 113 no longer pierces septum 112).

What is claimed is:

1. An infusion hub assembly, comprising:
   a wing having a hole passing therethrough;
   a circular hub received in the hole in the wing, the hub having a bore passing therethrough, with an upper portion of the circular hub having an attachment surface thereon;
   an infusion cannula extending downwardly away from the wing, the infusion cannula being in fluid communication with the bore passing through the hub;
   a cover having a bore passing therethrough and having an inner attachment surface adapted to mate with the attachment surface on the upper portion of the hub; and
   a septum positioned in alignment with the bore passing through the cover; and
   a housing with a downwardly pointing housing cannula and an infusion tube, the housing being attachable to the hub such that the housing cannula extends through the septum, and the housing and at least a portion of the infusion tube are rotatable with respect to the hub while permitting infusion from the infusion tube through the housing cannula into the infusion cannula;
   wherein the cover further comprises an outer attachment surface, the housing has an attachment surface adapted to mate with the outer attachment surface; and the attachment surface on the housing comprises a recess extending circumferentially around an internal surface of the housing.

2. The assembly of claim 1, wherein the upper portion of the hub is circular.

3. The assembly of claim 2, wherein the attachment surface on the upper portion of the circular hub comprises a lip extending circumferentially therearound.

4. The assembly of claim 1, wherein an underside surface of the wing comprises an adhesive layer.

5. The assembly of claim 1, wherein the hole in the wing is a stepped hole and the hub has a stepped outer dimension which fits into the stepped hole in the wing.

6. The assembly of claim 5, wherein both the stepped hole and the hub are circular and the hub has a stepped outer diameter.

7. The assembly of claim 1, further comprising:
a needle guide received in the bore of the hub.

8. The assembly of claim 7, wherein the needle guide is funnel shaped.

9. The assembly of claim 7, wherein the infusion cannula is attached to the needle guide.

10. The assembly of claim 1, wherein an upper portion of the cover is circular.

11. The assembly of claim 1, wherein the inner attachment surface on the cover comprises a recess extending circumferentially around an internal surface of the cover.

12. The assembly of claim 1, wherein the outer attachment surface on the cover comprises a lip extending circumferentially therearound.

13. The assembly of claim 12, further comprising:
a needle guide received in the bore of the hub, wherein the septum is received into the needle guide when the cover is attached to the hub.

14. The assembly of claim 12, further comprising:
an insertion needle configured to pass removably through the bore in the cover, the septum and the infusion cannula prior to attachment of the housing to the hub, wherein a distal end of the insertion needle extends downwardly out of a distal end of the infusion cannula when the insertion needle is fully advanced through the bore in the cover, the septum and the infusion cannula.

15. The assembly of claim 1, wherein the housing has a radial bore.

16. The assembly of claim 15, wherein:
the housing cannula passes at least partially through the radial bore in the housing, wherein a first end of the housing cannula is positioned to extend downwardly into the bores in the cover and hub when the housing is attached to the cover.

17. The assembly of claim 16, wherein:
the infusion tube is received into the radial bore of the housing.

* * * * *